(12) United States Patent
Malmsjo et al.

(10) Patent No.: US 9,708,416 B2
(45) Date of Patent: Jul. 18, 2017

(54) MICROSPHERES OF HYDROLYSED STARCH WITH ENDOGENOUS, CHARGED LIGANDS

(75) Inventors: Malin Malmsjo, Lund (SE); Eddie Thordarson, Bjarred (SE); Sten Peter Apell, Rostanga (SE); Peter Fyhr, Arkelstorp (SE)

(73) Assignee: Magle AB, Lund (CH)

( * ) Notice: Subject to any disclaimer, the term of this patent is extended or adjusted under 35 U.S.C. 154(b) by 303 days.

(21) Appl. No.: 13/513,656

(22) PCT Filed: Nov. 17, 2010

(86) PCT No.: PCT/SE2010/051268
§ 371 (c)(1),
(2), (4) Date: Jun. 4, 2012

(87) PCT Pub. No.: WO2011/068455
PCT Pub. Date: Jun. 9, 2011

(65) Prior Publication Data
US 2012/0244198 A1    Sep. 27, 2012

(30) Foreign Application Priority Data

Dec. 4, 2009 (SE) ........................ 0901521

(51) Int. Cl.
| | |
|---|---|
| *C08B 31/02* | (2006.01) |
| *A61F 13/00* | (2006.01) |
| *C12N 5/02* | (2006.01) |
| *A61K 9/00* | (2006.01) |
| *A61P 17/02* | (2006.01) |
| *C08B 31/00* | (2006.01) |
| *A61K 9/16* | (2006.01) |
| *A61K 31/718* | (2006.01) |
| *A61L 15/28* | (2006.01) |
| *A61L 24/08* | (2006.01) |
| *C08B 31/04* | (2006.01) |

(52) U.S. Cl.
CPC .......... *C08B 31/003* (2013.01); *A61K 9/1652* (2013.01); *A61K 31/718* (2013.01); *A61L 15/28* (2013.01); *A61L 24/08* (2013.01); *C08B 31/04* (2013.01); *A61L 2400/04* (2013.01); *A61L 2430/36* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 3,812,252 A | 5/1974 | Silvetti | |
| 5,079,354 A * | 1/1992 | Gross et al. | 536/111 |
| 5,736,371 A | 4/1998 | Samain et al. | |
| 5,939,100 A * | 8/1999 | Albrechtsen et al. | 424/489 |
| 5,968,794 A | 10/1999 | Samain et al. | |
| 6,060,461 A | 5/2000 | Drake | |
| 6,096,291 A * | 8/2000 | Betbeder et al. | 424/1.69 |
| 6,346,263 B1 * | 2/2002 | Mercier | A61K 9/5161 424/426 |
| 6,375,985 B1 * | 4/2002 | Bomberger et al. | 424/489 |

FOREIGN PATENT DOCUMENTS

| | | | |
|---|---|---|---|
| CN | 101121041 | 2/2008 | |
| CN | 101361986 | 2/2009 | |
| GB | 2402880 | * 12/2004 | ............ A01N 55/02 |
| JP | H06500570 | 1/1994 | |
| WO | 8904842 | 6/1989 | |
| WO | 9221329 | 12/1992 | |
| WO | 2009091549 A1 | 7/2009 | |
| WO | 2011068455 A1 | 6/2011 | |

OTHER PUBLICATIONS

Singla, A. K.; Chawla, M. "Chitosan: some pharmaceutical and biological aspects—an update" Journal of Pharmacy and Pharmacology, 2001, v. 53, 1047-1067.*
Extended European Search Report for PCT/SE2010/01268, Completed by the European Patent Office, Dated Sep. 25, 2013, 7 Pages.
Takagi et al. Journal of Bioscience and Bioengineering 1999, vol. 88, No. 6, p. 693-695, "Starch Particles Modified with Gelatin as Novel Small Carriers for Mammalian Cells."
International Seach Report for PCT/SE2010/051268, Completed by the Swdish Patent Office on Jan. 3, 2011, 7 Pages.
Rongved et al. "Starch microspheres as carriers for X ray imaging contract agents Synthesis and stability of new amino acid linker derivatives." Carbohydrate Research 1997, vol. 297, p. 325-331.
Taguchi, "Liver tumor targeting of drugs Spherex, a vascular occlusive agent", Gan to kagaku ryoho. Cancer and Chemotherapy, Jun. 1995, vol. 22, No. 7, p. 969-976.
Zhu et al. "Crosslinked Quaternary Ammonium Cornstarch Matrix for Slow Release of Carboxylic Groups containing Herbicides", Starch Starke 2000, vol. 52, No. 2-3, p. 58-63.
Alexandru et al. "Cross Linked Starch Derivatives for Highly Loaded Pharmaceutical Formulations", American Chemical Society 2006, Chapter 6, p. 121-137.
Tomasik et al. "Chemical Modification of Starch", Advances in Carbohydrate Chemisty and Biochemistry 2004, vol. 59, p. 175 and 212-218.
Sathe et al. "Isolation, Partial Characterization and Modification of the Great Northern Bean Phaseolus vulgaris L. Starch", Journal of Food Science 1981, vol. 46, p. 617-621.

(Continued)

*Primary Examiner* — Sue Liu
*Assistant Examiner* — Erin Hirt
(74) *Attorney, Agent, or Firm* — Ballard Spahr LLP

(57) ABSTRACT

Biodegradable microspheres having a diameter of 10-2000 µm having cross-linked hydrolysed starch onto which at least one type of ligand has been coupled via a carboxylic ester bond. The ligand shall be an endogenous, charged molecule with a molecular mass of less than 1000 Da having at least one additional carboxylic acid function in addition to the one utilised for coupling the ligand to the microsphere and/or at least one amine function. On average 0.05-1.5 ligands are coupled to each glucose moiety in the hydrolysed starch.

13 Claims, 5 Drawing Sheets

(56) References Cited

OTHER PUBLICATIONS

Hui et al. "Preparation and properties of octenyl succinic anhydride modified potato starch", Food Chemistry 2009, vol. 114, p. 81-86.
Ratnoff et al. "Interactions among Hageman factor, plasma prekallikrein, high molecular weight kininogen, and plasma thromboplastin antecedent", Medical Sciences Feb. 1979, vol. 76, No. 2, p. 958-961.
Manousos et al. "Feasibility Studies of Oncornavirus Production in Microcarrier Cultures", In Vitro 1980, vol. 16, No. 6, p. 507-515.
Lee et al. "Platelet adhesion onto chargeable functional group gradient surfaces", Platelet adhesion onto gradient surfaces 1998, p. 180-186.
Australian Office Action for Australian Application No. 2010327380, Date of Issue May 23, 2014, 3 Pages.

\* cited by examiner

MICROSPHERES OF HYDROLYSED STARCH WITH ENDOGENOUS, CHARGED LIGANDS

CROSS-REFERENCE TO RELATED APPLICATION

This application is the U.S. national phase of PCT Appln. No. PCT/SE2010/051268 filed on Nov. 17, 2010, which claims priority to SE Patent Application No. 0901521-5 filed on Dec. 4, 2009, the disclosures of which are incorporated their entirety by reference herein.

TECHNICAL FIELD

The present invention relates to biodegradable microspheres of hydrolysed starch with endogenous, charged ligands attached thereto. The invention also relates to a material comprising such microspheres, and to use of the microspheres or the material in hemostasis, wound healing, cell culture or vascular embolisation.

BACKGROUND OF THE INVENTION

Starch, a branched glucose polymer ($\alpha$4-glucose chains with $\alpha$6 branches), is a natural material found in plants and animals where it functions as an energy store. The polymer consists of amylose (long chained and lowbranched) and amylopectin (highly branched and short chained).

Degradable starch microspheres (DSM) are formed of cross-linked starch chains. Degradable starch microspheres have been used for temporary vascular occlusion both with and without the co-administration of cytotoxic drugs (treatment of tumours and prevention of haemorrhages) for many years, but are also used for topical and intraoperative hemostasis.

The starch microspheres are degraded in vivo by plasma amylase into oligosaccharides, maltose and eventually to glucose that enter the normal metabolism.

Microparticles of starch or modified starch have been shown in prior art, for example in U.S. Pat. No. 6,060,461 and WO 2009/091549, i.a. for biocompatible hemostasis.

Furthermore U.S. Pat. No. 3,812,252 relates to hydrolysed starch and the use thereof for treating wounds, including chronic ones.

Wound healing is the intricate process in which the skin or another organ repairs itself after injury. The classic model of wound healing is divided into four sequential, yet overlapping, phases: (1) hemostatic, (2) inflammatory, (3) proliferative and (4) remodelling.

Hemostasis is the primary phase in wound healing, which causes the bleeding process to stop. Within minutes from injury to the skin or other organ, platelets (thrombocytes) are activated and aggregate at the injury site to form a fibrin clot.

When endothelial injury occurs, the endothelial cells cease to inhibit coagulation and begin to secrete coagulation factors that induce hemostasis after injury. Hemostasis has three major steps: 1) vasoconstriction, 2) temporary blockage by a platelet plug, and 3) blood coagulation by conversion of fibrinogen to fibrin and formation of a clot that seals the hole until tissues are repaired.

In the inflammatory phase, bacteria and debris are phagocytised and removed, and factors are released that cause the migration and division of cells involved in the proliferative phase.

In about 2-3 days fibroblasts begin to enter the wound site, marking the onset of the proliferative phase even before the inflammatory phase has ended. This phase is characterised by angiogenesis, collagen deposition, granulation tissue formation, epithelialisation, and wound contraction. In angiogenesis new blood vessels are formed, necessary for the supply of oxygen and nutrients to the wound site for supporting later wound healing stages. Simultaneously, fibroblasts begin accumulating in the wound site, their number peaking at 1 to 2 weeks post trauma. By the end of the first week, fibroblasts are the main cells in the wound.

In the first 2 or 3 days after injury, fibroblasts mainly proliferate and migrate, while later, they are the main cells that lay down the collagen matrix in the wound site. Initially fibroblasts use the fibrin scab formed in the inflammatory phase to migrate across, adhering to fibronectin. Fibroblasts then deposit ground substance into the wound bed, and later collagen, which they can adhere to for migration. Granulation tissue, growing from the base of the wound, begins to appear in the wound already during the inflammatory phase, and continues growing until the wound bed is covered. Granulation tissue consists of new blood vessels, fibroblasts, inflammatory cells, endothelial cells, myofibroblasts, and the components of a new, provisional extracellular matrix. Re-epithelialisation of the epidermis occurs when epithelial cells proliferate and "crawl" atop the wound bed, providing cover for the underlying newly formed tissue.

Cell culture is the process by which cells are grown under controlled conditions. The historical development and methods of cell culture are closely interrelated to those of tissue- and organ culture. Animal cell culture became a common laboratory technique in the mid-1900s, but the concept of maintaining live cell lines separated from their original tissue source was discovered in the 19th century. Tissue culture is the growth of tissues and/or cells separate from the organism. This is typically facilitated via use of a liquid, semi-solid, or solid growth medium, such as broth or agar. In this specification cell culture and tissue culture will be used synonymously.

Some cells naturally live in suspension, without being attached to a surface, such as cells that exist in the bloodstream. Those cells can be grown in suspension. However, most cells derived from solid tissues are anchor dependent, so called adherent cells. Adherent cells require a surface, such as tissue culture plastic or a microcarrier, to grow on. Microcarriers for growing adherent cells are available, for example dextran microspheres. When adherent cells are harvested or passaged (transport of subculture), the cells need to be detached from the surface it has grown on. Commonly this is done by the addition of a mixture of trypsin-EDTA to the culture.

Vascular embolisation (occlusion) is used as a minimally-invasive alternative to surgery. The purpose of embolisation is to prevent blood flow to an area of the body, creating ischemia, which effectively can shrink a tumour or block an aneurysm.

The procedure is carried out as an endovascular procedure, by a consultant radiologist in an interventional suite. It is common for most patients to have the treatment carried out with little or no sedation, although this depends largely on the organ to be embolised.

Access to the organ is gained by means of a guidewire and catheter(s). The artificial embolus used is usually one of the following methods: coil or hydrocoil, particles, foam or plug.

Agents used in embolisation therapy are i.a. liquid embolic agents which are able to flow through complex vascular structures. Examples of such are ethiodol, made from iodine and poppyseed oil which is a highly viscous agent and is usually used for chemoembolisations, especially for hepatomas; sclerosing agents, which will harden the endothelial lining of vessels and ethanol.

Particulate embolic agents, are also used to embolise precapillary arterioles or small arteries. Gelfoam® temporarily occludes vessels for 5 weeks. Microspheres are commonly used agents for both bland embolisation and chemoembolisation. Polyvinyl alcohol (PVA) and acrylic gelatin microspheres are not degradable in-vivo, hence they remain permanently in the patient. Depending on the situation, different sizes of microspheres are used, ranging from about 50 μm to about 1.2 mm in diameter.

SUMMARY OF THE INVENTION

In some cases it may be of interest to alter the properties of biodegradable starch microspheres. The present invention provides ways of altering the biodegradability of the biodegradable starch microspheres; the affinity of the biodegradable starch microspheres to biological systems and/or its components; the degree of swelling of the biodegradable starch microspheres; the rate of swelling of the biodegradable starch microspheres; the compressibility/elasticity of the biodegradable starch microsphere and/or the selectivity of chemical interaction with ions and molecules in and on the biodegradable starch microsphere. The biological system and/or its components described above can for example constitute an organ or cell or any of their components; bacteria; viruses; proteins and enzymes; polysaccharides; lipids; small molecules and/or ions.

Thus, the present invention relates to a biodegradable microsphere having a diameter of 10-2000 μm comprising cross-linked hydrolysed starch onto which at least one type of ligand has been coupled via a carboxylic ester bond, wherein said ligand is an endogenous, charged molecule with a molecular mass of less than 1000 Da comprising at least one additional carboxylic acid function and/or at least one amine function, and wherein on average 0.05-1.5 ligands have been coupled to each glucose moiety in the hydrolysed starch.

The present invention also relates to different uses and applications of this microsphere.

DESCRIPTION OF THE INVENTION

The microspheres according to the invention comprise cross-linked acid hydrolysed starch. The microspheres may be manufactured from acid hydrolysed starch by emulsifying a starch solution in an organic solvent, such as toluene or ethylene dichloride. The poly-glucose chains are cross-linked with a cross-linking reagent such as epichlorohydrin, forming glycerol ether (1,3-oxy-propan-2-ol) links, as shown below, forming degradable starch microspheres (DSM).

DSM are degraded in vivo by amylase to oligodextrins and eventually to glucose. Cross-links remain as oligosaccharides of variable size. The fate of these in vivo is currently unknown, but it is likely that they are either excreted in the urine or filtered of to the reticuloendothelial system and degraded.

The microspheres are biodegradable, defined as a material that is degraded and/or metabolised and excreted under physiological (in vivo) conditions. In this case physiological (in vivo) comprises animals, more specifically, verterbrates and most specifically mammals.

Essentially, the biodegradable starch microspheres are fully degraded and eliminated from its physiological environment, such as the human body. Depending on the application, the microspheres are tailored to be degraded in a certain time suitable for its intended use. This time can range from minutes up to 3 months, more preferably up to 1 month.

The size of the biodegradable microsphere according to the invention is in the micro scale, and more particular from 10 μm to 2000 μm.

The properties of the DSM may be altered by attaching ligands to the DSM, and more particularly to the hydroxyl groups of the glucose. The properties of DSM are affected by the choice of ligands and also by the number of ligands attached to the starch.

The ligands are attached to the DSM by coupling it via a carboxylic ester bond to the glucose monomers of the DSM. To enable attachment of the ligands to the hydrolysed starch via this ester bond, the ligands shall comprise at least one carboxylic acid function, i.e. at least one —COOH group, capable of forming an ester bond. The ester bond is hydrolysable, by chemical and or enzymatic hydrolysis in vivo, and the utilisation of such an ester bond results in a biodetachable ligand.

Furthermore, the ligands shall be endogenous substances that are charged at a physiological pH, i.e. at pH 6-8. In addition to the carboxylic acid function utilised to enable attachment of the ligand to the hydrolysed starch via an ester bond, the ligands shall comprise at least one additional carboxylic acid function and/or at least one primary, secondary, ternary or quarternary amine function. As the ligands are endogenous compounds, the DSM thus degrades into endogenous compounds that are metabolised and/or excreted.

The ligand may thus be positively charged, negatively charged or zwitter-ionic, i.e. both positively and negatively charged at the same time. The ligands may also have unpolar (hydrophobic) parts to further modify the properties of the

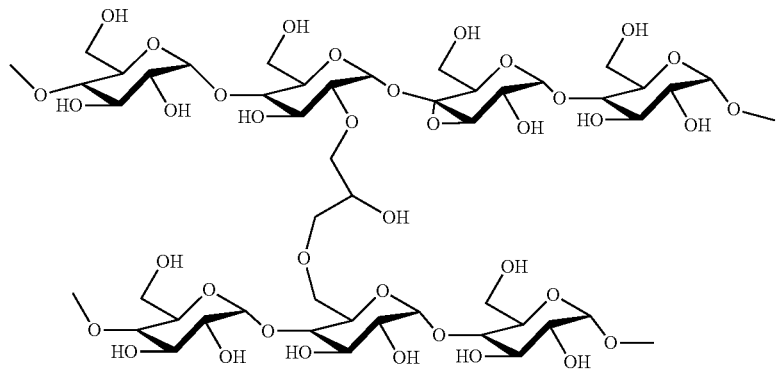

DSM. It is further possible to use a mixture of different ligands.

Charged ligands require a counter ion. When the ligand is positively charged, the counter ion will be negatively charged, and when the ligand is negatively charged, the counter ion will be positively charged. This counter ion may be a physiologically active counter ion. When the ligand is zwitter-ionic, it constitutes its own counter ion.

The endogenous ligands shall further be small molecules with a molecular mass of less than 1000 Da.

To each glucose moiety in the DSM 0.05-1.5 ligands, on average, may be coupled according to the invention. The molar ratio of ligand to glucose is thus from 1.5:1 to 1:20 in the DSM.

The ligand may be selected from the group consisting of amino acids, other nitrogen containing organic acids and dioic acids.

Ligands that may be preferred for some embodiments of the invention are listed in Table 1.

Table 1 showing preferred ligands. R in the structures represents a glucopyranosyl monomer, shown below, in the hydrolysed starch. $R^2$ represents a ligand, in any of its possible positions 2, 3 and/or 6, on the glucose moiety of DSM as shown below.

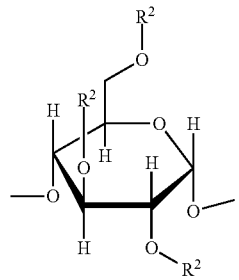

| Amino acids as $R^2$ | Charge | Properties | Structure |
|---|---|---|---|
| Arginine | 2+ | polar | 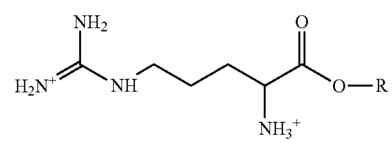 |
| Histidine | + (10%) | polar | 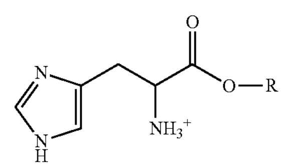 |
| Lysine | 2+ | polar | 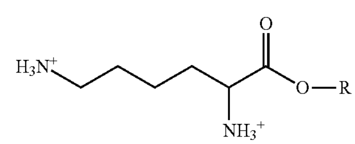 |
| Glycine | + | polar | 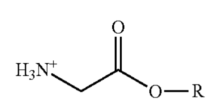 |
| Proline | + | | 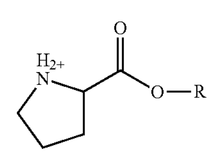 |
| Alanine | + | hydrophobic | 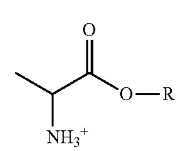 |

-continued

Table 1 showing preferred ligands. R in the structures represents a glucopyranosyl monomer, shown below, in the hydrolysed starch. $R^2$ represents a ligand, in any of its possible positions 2, 3 and/or 6, on the glucose moiety of DSM as shown below.

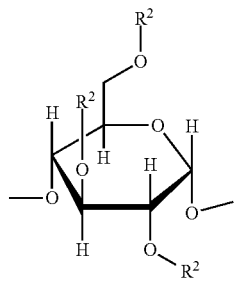

| Isoleucine | + | hydrophobic | |
| Leucine | + | hydrophobic | |
| Phenylalanine | + | hydrophobic | |
| Tryptophan | + | hydrophobic | |
| Tyrosine | + | hydrophobic | |
| Valine | + | hydrophobic | |
| Serine | + | polar | |
| Aspargine | + | | |

-continued

Table 1 showing preferred ligands. R in the structures represents a gluco-pyranosyl monomer, shown below, in the hydrolysed starch. $R^2$ represents a ligand, in any of its possible positions 2, 3 and/or 6, on the glucose moiety of DSM as shown below.

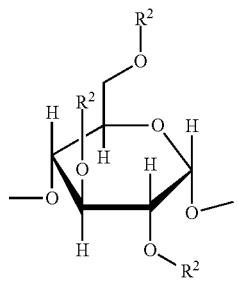

| | Charge | Properties | Structure |
|---|---|---|---|
| Glutamine | + | polar | 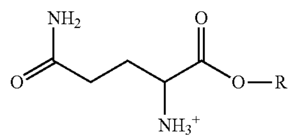 |
| Threonine | + | polar | 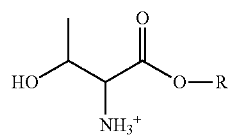 |
| Glutamic acid | ± | polar | 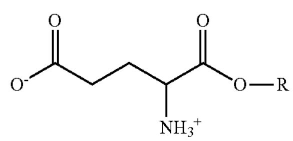 |
| Aspartic acid | ± | polar | 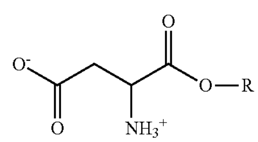 |

| Acids as $R^2$ | Charge | Properties | Structure |
|---|---|---|---|
| Succinic acid | − | | 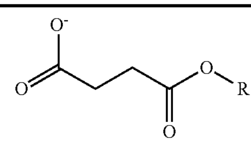 |
| Adipic acid | − | | 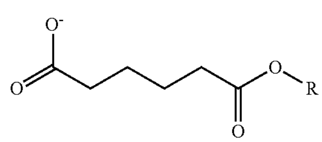 |
| Oxalic acid | − | | 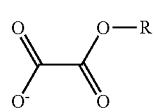 |
| Citric acid | 2− | | 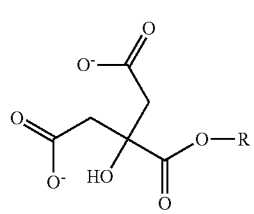 |

-continued

Table 1 showing preferred ligands. R in the structures represents a glucopyranosyl monomer, shown below, in the hydrolysed starch. $R^2$ represents a ligand, in any of its possible positions 2, 3 and/or 6, on the glucose moiety of DSM as shown below.

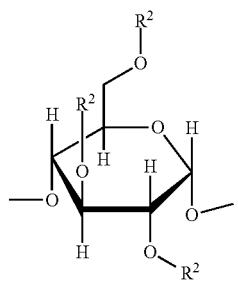

| | | | |
|---|---|---|---|
| Tartaric acid | – | | |
| Maleic acid | – | | |
| Malonic acid | – | | |

| Nitrogen containing organic acids as $R^2$ | Charge | Properties | Structure |
|---|---|---|---|
| Betaine | + | | 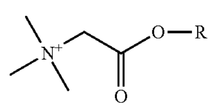 |
| Carnitine | + | | 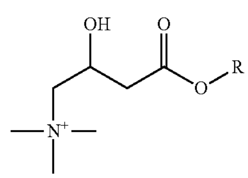 |
| Creatine | + | | 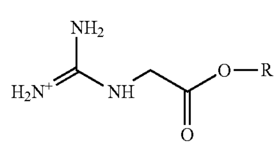 |
| Methylglycine | + | | 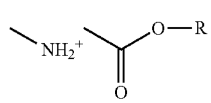 |
| Dimethylglycine | + | | 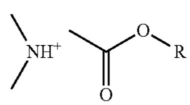 |

The above described microsphere may be used in hemostasis, wound healing, cell culture in vitro and vascular embolisation. The above described microsphere may also be used to produce a biodegradable material suitable for use in wound healing.

These different applications are discussed further below.

Hemostasis

In some embodiments for use in hemostasis, the ligands attached to the microspheres are preferably positively charged or zwitter-ionic.

In some embodiments, the ligands attached to the microspheres are preferably positively charged. The counter ion used may then be ellagic acid.

For hemostasis, the microspheres according to the invention shall preferably have a mean diameter of from 10 µm to 200 µm.

When used for hemostasis, the microspheres according to the invention can be added onto/into the wound as a powder, in a solution or adhered to a backing structure, such as gauze.

Wound Healing

For wound healing, the microspheres may be used to produce a material. This material shall have a three-dimensional structure consisting of the microspheres and voids between the microspheres.

Due to the voids, the material will be permeable for both gases and liquids, and thus non-gelling when in contact with liquids.

The fact that the material is a non-gelling material means that it is possible to avoid a film forming layer when using the material on/in a wound, and thereby that it is possible to prevent oedema to collect under the layer; facilitate efficient transport of oxygen and nutrients and further that unobstructed migration of cells and efficient transduction of pressure to or from the underlying tissue is allowed.

The microspheres in the material may be of a homogenous size fraction. To establish voids in between the microspheres it is in many cases preferred that the microspheres in the material have a fairly uniform size. If the microspheres should have a non-uniform size the voids would be filled up by smaller microspheres thereby creating a more solid structure which will be deleterious to the material's intended effect. When the microspheres form part of a homogenous size fraction, the size of the microspheres should, at least for some embodiments, not differ more than up to ±15% from the median. For example, in a fraction of 300 µm microspheres, the individual microspheres may be from 255 up to 345 µm. The size of the voids, i.e. the space between round spheres of a uniform size packed together, may be calculated as $((2/\sqrt{3})-1) \approx 0.155$ times the diameter of the microspheres.

The material may consist of a one-piece, solid, porous and three-dimensional network.

The microspheres may be attached to a substrate backing, thereby immobilising the microspheres. Such a backing can be an ordinary gauze or a polymeric foam material.

At least for some embodiments for use in wound healing, the ligands attached to the microspheres are preferably positively charged.

At least for some embodiments for use in wound healing, the ligands attached to the microspheres are preferably positively charged and hydrophobic.

For wound healing the microspheres according to the invention preferably have a mean diameter of from 200 µm to 2000 µm.

Preferably the voids in the material have a diameter of from 30 µm to 300 µm, and more preferably from 100 µm to 300 µm. The voids shall be at least 30 µm, since this allows for the passage of tissue cells and nerve cell bundles that are typically 20-30 µm in diameter.

Furthermore, the material's surface characteristics stimulate cell adherence and proliferation. This involves cell affinity to the material surface and a material elasticity that is suitable for adherence.

The biodegradable material suitable for wound healing according to the invention enhances in particular cell attachment, migration, and proliferation, either in standard wound healing management or in NPWT (Negative Pressure Wound Treatment) procedures specifically for the third and fourth phases of the wound healing process, viz the proliferative and remodelling phases.

The three-dimensional structure of the biodegradable material suitable for wound healing according to the invention decreases the formation of scar tissue. Realising that scar tissue is characterised by a rather unidirectional deposition of collagen, a matrix able to force a disorganised deposition of collagen is likely to decrease scarring. Collectively, the material according to the present invention stimulates and facilitates permanent in-growth of new and healthy granulation tissue.

In wound healing it may be advantageous to delay the biodegradability of the material by up to between 2 days and 2 weeks, by selecting the appropriate ligand(s). This allows for an adequate healing without a need for the change of the dressing if not so needed for other reasons.

When used in wound healing or wound management, the material according to the invention can be added onto/into the wound as a powder, in a solution, adhered to a backing structure, such as gauze or as a solid one-piece network.

The material according to the invention may also form part of a wound dressing.

It has been shown that when applying a 2 mm layer of non-gelling biodegradable starch spheres of a mean diameter of 200 µm having a positively charged surface to a wound bed a very good granulation is obtained with a growth of cells up to 500 µm in four days.

In Vitro Cell Culture

For use in cell culture in vitro, the microspheres preferably have a mean diameter of from 200 µm to 1000 µm, more preferably between 200 µm and 500 µm.

For some embodiments for in vitro cell cultures, the ligands are preferably positively charged.

The voids are important for cell cultures as they allow an effective passage for adherent and growing cells and also allow an effective transportation of growth matrix and larger molecules within the culture.

Vascular Embolisation

For vascular embolisation, the microsphere according to the invention preferably has a mean diameter of from 10 µm to 1200 µm.

For use in vascular embolisation, the ligands attached to the microspheres are preferably negatively charged, at least in some embodiments.

The negative charge may be used to ionically bind a cationic cytostatic drug, which then constitute the counter ion, for the treatment of tumours.

Such cytostatic drugs include doxorubicin, irinotecan, topotecan, epirubicin, mitomycin, cisplatin and sorafenib.

The microspheres according to any of the embodiments of the invention as described above and as specified in the claims may be used in methods for enhancing, facilitating or carrying out hemostasis, wound healing and/or vascular embolisation. Similarly, the material according to any of the embodiments of the invention as described above and as specified in the claims may be used in a method for facilitating or carrying out wound healing.

The microspheres or material, respectively, is then administered in an effective amount to a mammal, such as a human, in need of hemostasis, wound healing and/or vascular embolisation. It may be a human suffering from a bleeding wound or some other type of wound, either internally or externally, such as on the skin.

By "administration" is intended that the microspheres or the material according to the invention is brought into contact with the area where hemostasis, wound healing and/or vascular embolisation is needed. In the case of a wound, for hemostasis or wound healing purposes, the material may, for example, be placed in the cavity of the wound or on the wound surface. In the case of wound healing the DSM may be formulated as a powder, suspension or ointment. In the case of hemostasis the DSM may be applied as a dry powder or incorporated in a gauze or in a pad. In the case of embolisation the DSM are preferably suspended in a suitable medium such as physiological saline.

In this context "effective amount" means an amount that will have a positive effect on hemostasis, wound healing and/or vascular embolisation.

The microspheres according to the invention may also be used in methods for enhancing, facilitating or carrying out in vitro cultivation of cells. The microsphere according to the invention may then be added to an appropriate culture medium. The cells to be cultivated are also added to this culture medium. The microspheres may be added to the culture medium simultaneously with the cells, before the addition of the cells or after the addition of the cells. The cells are then allowed to propagate. As explained above, cell culture in this specification also includes tissue culture.

The microspheres according to any of the embodiments of the invention as described above and as specified in the claims may further be used in enhancement, facilitatation or to carry out hemostasis, wound healing and/or vascular embolisation.

The microspheres according to any of the embodiments of the invention as described above and as specified in the claims may further be used for the production of a medical device or a pharmaceutical composition.

The microspheres according to any of the embodiments of the invention as described above and as specified in the claims may further be manufactured specifically for use in enhancement, facilitatation or to carry out hemostasis, wound healing and/or vascular embolisation.

Throughout the description and the claims, the words "comprise" and "contain", and variations of the words, for example "comprising" and "comprises", mean "including but not limited to", and they are not intended to exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

The invention is described in more detail below in the Examples, which refer to the appended drawings on which.

$$Y = Y_\infty (1 - e^{-kt})$$

wherein k=the first-order swelling constant, and $Y\infty$=the volume increase at maximum swelling.

Figure 3:
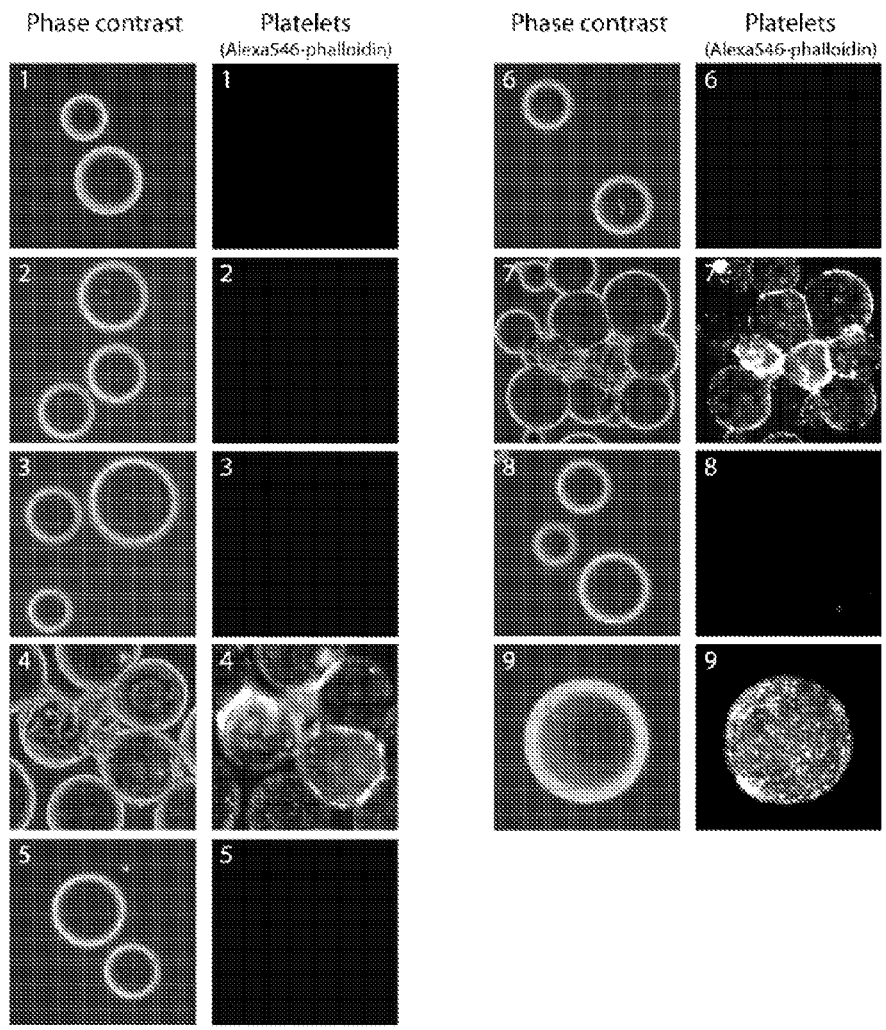
Figure 3:
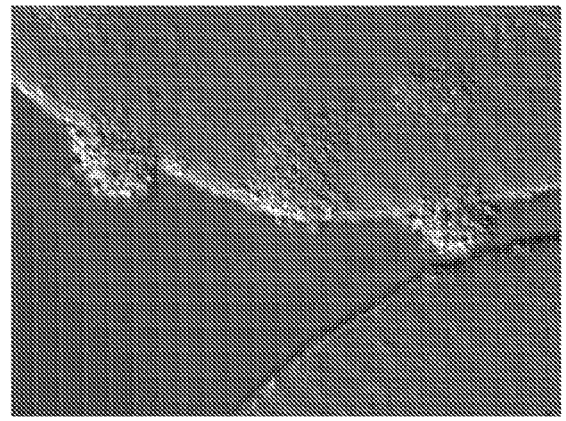

FIG. 3 illustrates platelet adhesion. FIG. 3 A shows phase contrast and fluorescent micrographs showing the DSM and DSM-adhered platelets according to the different modified batches. FIG. 3. B shows close-ups of the junction between two aggregated DSM (batch 4) and the platelet aggregates attached to the DSM. Imaged using differential interference contrast (DIC) microscopy.

Figure 4:
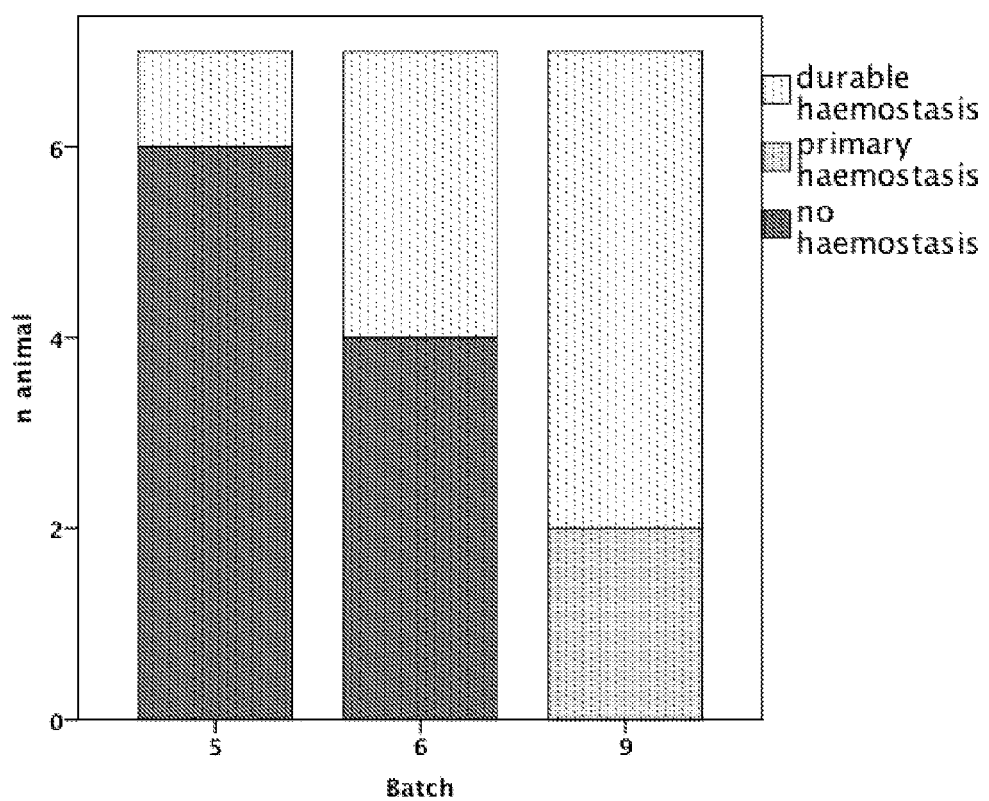

FIG. 4 illustrates an in vivo study of three of the DSM batches. Batches 5, 6 and 9 were evaluated in an experimental bleeding model (renal trauma) in anti coagulated rats. All animals treated with batch 9 obtained primary hemostasis, 29% re-bled within 20 min observation. The other batches demonstrated significantly less hemostatic efficiency with few animals achieving primary hemostasis.

Figure 5:
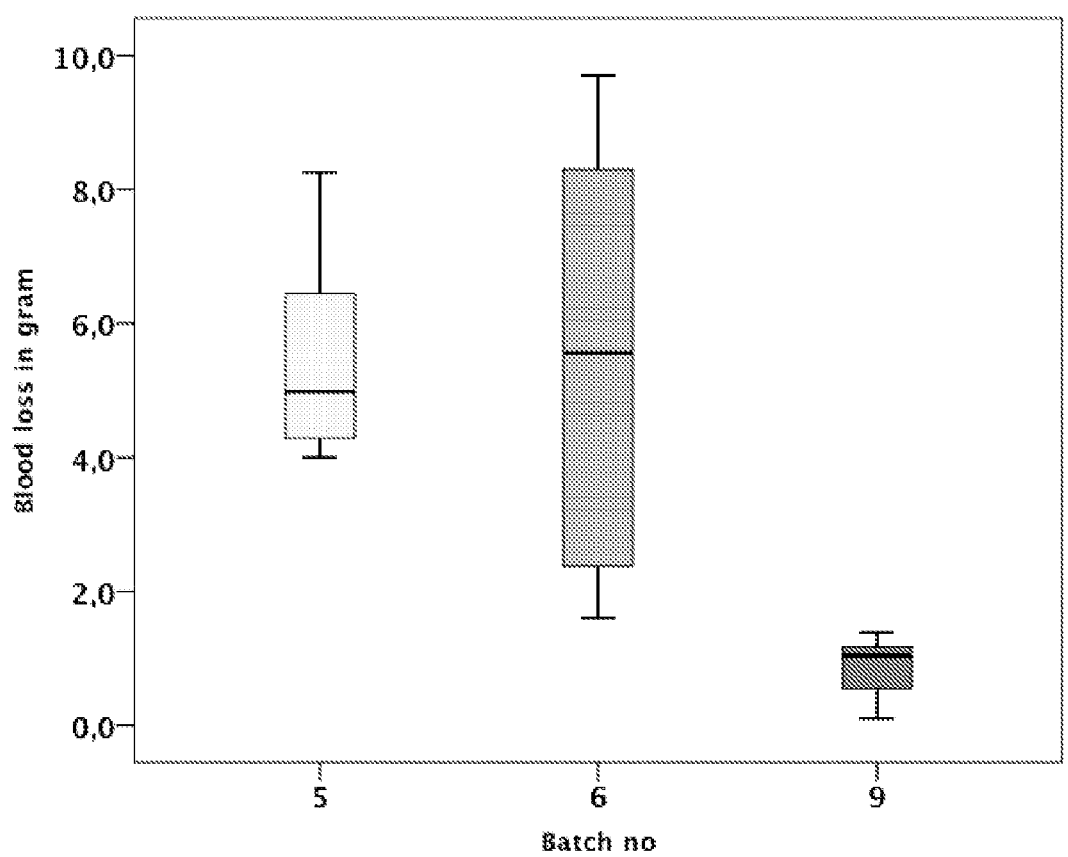

FIG. 5 illustrates blood loss according to treatment batch in the experimental in vivo study. Blood loss was measured by weighing the excessive blood collected in gauze. There was a significant difference in blood loss between the different batches (p=0.001), where batch 5 was unmodified DSM, batch 6 proved activation of the coagulation and DSM in batch 9 adsorbed platelets.

EXAMPLES

The degradable starch microspheres (DSM) were prepared by emulsion, cross-linking of hydrolysed starch with epichlorohydrin in toluene. The DSM are subsequently washed repeatedly with ethanol followed by distilled water and finally successively dehydrated with increasing concentrations of ethanol and finally dried over night at 60° C.

Details on Preparation of the DSM 2 g of sodium hydroxide is dissolved in 280 mL purified water and 2 g sodium borohydride is added and dissolved. 153 g of hydrolysed starch is dissolved by slow stirring for at least 2 hours. 20 g of surfactant (Rhodafac PA17) is dissolved in 450 g toluene. The starch solution is then added and emulsified in the toluene solution, the temperature is increased to 70° C. and the emulsion is stirred until the desired droplet size distribution has been attained. 22 g of epichlorohydrin is added and crosslinking is performed for 5 hours. The mixture is cooled to room-temperature and allowed to sediment whereafter the supernatant is decanted. The DSM are given three washes with 95% ethanol, one wash with 0.8% acetic acid, followed by 4 washes with purified water and finally dyhydrated with absolute ethanol before drying at 60° C. in a ventilated drying cabinet.

Determination of Degree of Substitution (DS)

The degree of substitution is defined as the average number of substitutes per glucose monomer.

The method of alkali saponification, followed by titration of the excess of alkali was employed for the determination of the degree of substitution. To a sample of 250 mg of DSM 10 mL of 0.50 M NaOH was added and this was allowed to stand at room temperature for 72 h with occasional shaking. The excess of NaOH was titrated with 0.50 M HCl using phenolphthalein as indicator.

Determination of Degradability with Amylase

A sample of DSM (3-6 mg) was diluted with phosphate buffer, pH 7 (5 ml) and then 400 µl human saliva was added, followed by incubation at 37° C. for 4 h. The sample was allowed to stand for 20 min or was centrifuged and then a small sample was taken from the bottom and analysed by microscope to determine the presence or absence of microspheres.

General Procedure for Substitution of DSM with Dioic Acids (Examples Listed in Table 1)

DSM (1 g) was suspended in DMF (10 ml), to this mixture succinic anhydride (154 mg, 1.54 mmol) and pyridine (124 µl, 1.60 mmol) were added. The mixture was stirred and heated to 90° C. over night and then the material was washed three timed with 40 ml of ethanol followed with 5 ml saturated NaHCO$_3$ and then three times with 30 ml of water. The material was dehydrated with ethanol and dried in an oven at 60° C. The material was analysed with FTIR showing ester carbonyl at 1730 cm$^{-1}$.

DS: 0.25 (determined as described above).

Degradable by α-amylase (determined as described above).

General Procedure for Substitution of DSM with Esters

Modification with Betaine

Betaine (1.66 g, 10.8 mmol) and CU (1.75 g, 10.8 mmol) were mixed with 50 ml of DMF and heated to 80° C. for 2 h. Then DSM (5 g) was added and the temperature was raised to 90° C. and the mixture was stirred over night. The mixture was washed with ethanol (250 ml) two times, diluted hydrogen chloride (250 ml) and two times with water (250 ml). The material was dehydrated with ethanol and dried over night at 60° C.

FTIR showing ester carbonyl at 1751 cm$^{-1}$.

DS: 0.23 (determined as described above).

Degradable by α-amylase (determined as described above).

Modification with Dimethyl-Glycine

As in the example with betaine above, but DSM (2 g), N,N-Dimethylglycine hydrochloride (430 mg, 3.1 mmol) and CDI (500 mg, 3.1 mmol) were used FTIR showing ester carbonyl at 1753 cm$^{-1}$.

DS: 0.24 (determined as described above).

Degradable by α-amylase (determined as described above).

Modification with N$_\alpha$-Acetyl-L-Arginine

As in the example with betaine above, but DSM (2 g), N$_\alpha$-Acetyl-Larginine (623 mg, 2.5 mmol), CDI (400 mg, 2.5 mmol) were used.

FTIR showing ester carbonyl at 1748 cm$^{-1}$.

DS: 0.24 (determined as described above).

Degradable by α-amylase (determined as described above).

Modification with Proline

As in the example with betaine above, but DSM (1 g), Boc-Pro-OH (266 mg, 1.2 mmol), CDI (200 mg) were used followed by deprotecting of the tert-butoxycarbonyl with TFA.

FTIR showing ester carbonyl at 1743 cm$^{-1}$.

Degradable by α-amylase (determined as described above).

Modification with Glycine

As in the example with betaine above, but DSM (1 g), Boc-Gly-OH (216 mg, 1.2 mmol), CDI (200 mg) were used followed by deprotecting of the tert-butoxycarbonyl with TFA.

FTIR showing ester carbonyl at 1748 cm$^{-1}$.

Degradable by α-amylase (determined as described above).

Modification with Phenylalanine

As in the example with betaine above, but DSM (1 g), Boc-Phe-OH (327 mg, 1.2 mmol), CDI (200 mg) were used followed by deprotecting of the tert-butoxycarbonyl with TFA.

FTIR showing ester carbonyl at 1743 cm$^{-1}$.

Degradable by α-amylase (determined as described above).

Non-Detatchable Surface Modifications Used in Investigation of Charge Effects

Figure 1:
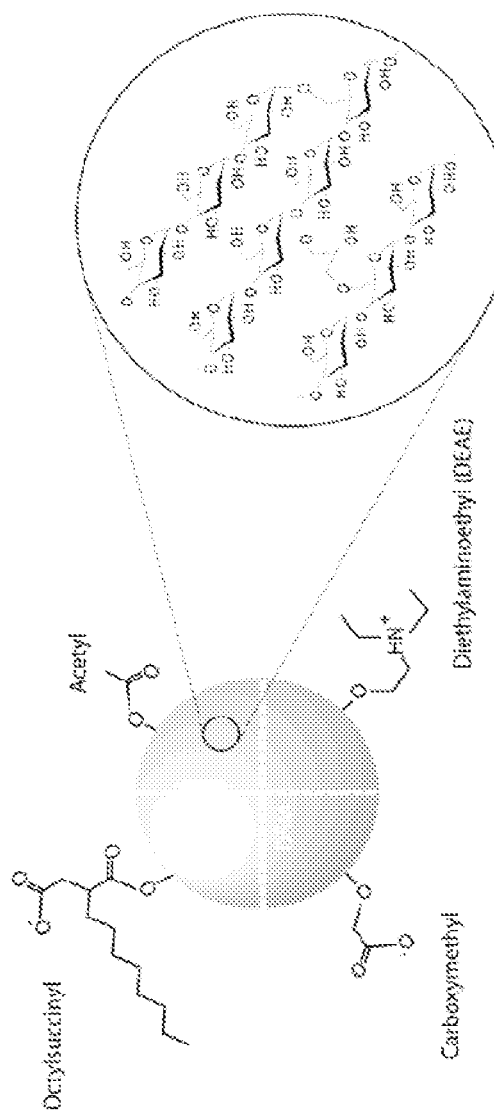
FIG. 1 is a schematic picture of a degradable starch microsphere (DSM) and the chemical modifications performed in this study.

The surface modifications are illustrated in FIG. 1.

Octenylsuccinate (Negative and Hydrophobic)

80 g of DSM were suspended in purified water, N-octenyl succinic anhydride (Pentagon) was added to 0.08 g/g dry DSM and the reaction was continued for 3 h. A pH above 7.4 was maintained by additions of 0.75 M NaOH. The resulting material was washed 8 times with 2000 mL of purified water and thereafter dehydrated with increasing concentrations of ethanol and finally dried over night at 60° C. (Hui Rea. Preparation and properties of octenyl succinic anhydride modified potato starch. Food Chemistry 2009; 114:81-6).

Carboxymethylation (Negative)

50 g of DSM were suspended in purified water; chloroacetic acid was added to 0.1 g/g dry DSM and the reaction were continued for 5 h at 70° C. Before adding the chloroacetic acid it was dissolved in water and neutralised with 1 M NaOH. The resulting material was washed 6 times with 2000 mL of purified water and thereafter dehydrated with increasing concentrations of ethanol and finally dried over night at 60° C. (Tomaski P, Schilling, C. H. Chemical modification of starch. Adv Carbohyd Chem Biochem 2004; 59:175-403).

Acetylation (Hydrophobic)

50 g of DSM were suspended in purified water, acetic anhydride was added to 0.05 g/g dry DSM. Acetic anhydride was added drop by drop and a pH between 7.3 and 7.8 was maintained by additions of 0.75 M NaOH. The resulting material was washed 7 times with 2000 mL of purified water and thereafter dehydrated with increasing concentrations of ethanol and finally dried over night at 60° C. (Sathe S K, Salunkhe, D. K. Isolation, Partial Characterisation and Modification of the Great Northern Bean (Phaseolus vulgaris L.) Starch. J Food Sci 1981; 46:617-21).

Diethylaminoethyl Chloride, Aldrich (Positive)

50 g of DSM were suspended in purified water, 0.375 mol of DEAE hydrochloride was added and the temperature was increased to 60° C. 250 ml of 3 M sodium hydroxide solutions was added and the reaction was maintained at 60° C. for one hours. The DSM was than washed with 20 L of purified water in a Büchner funnel. The DSM was then dehydrated and dried as above (Manousos M, Ahmed M, Torchio C, Wolff J, Shibley G, Stephens R, et al. Feasibility studies of oncornavirus production in microcarrier cultures. In Vitro 1980 June; 16(6):507-15).

Ellagic Acid (Adsorbed/Absorbed Negative)

Ellagic acid (Alfa Aesar) was passive adsorbed using two different methods. Method 1: 0.1 mM ellagic acid was dissolved in water and then mixed with the DSM. Method 2: 0.1 mM ellagic acid was dissolved in ethanol and then mixed with the DSM (Ratnoff O D, Saito H. Interactions among Hageman factor, plasma prekallikrein, high molecular weight kininogen, and plasma thromboplastin antecedent. Proc Natl Acad Sci USA 1979 February; 76(2):958-61). Washing and drying as above. The ellagic acid was passively absorbed/adsorbed and was not applicable for measurement of charges.

The different surface modifications were produced with standard modification protocols (not optimised). The modifications were selected for proving the concept of a hemostatic effect in vitro and in vivo, and were not assessed for being toxicologically acceptable in humans.

Surface Charge

The degree of surface charge was measured by a PCD 02, Particle Charge Detector (Mütek).

Design

The nine different modified DSM were randomised and blinded. No information about the modifications was sent to the performers of the studies.

Characterisation of DSM

The morphology of the starch microspheres was determined by observation in microscope (AxioObserver Z1, Zeiss), and sphere diameters were measured for a minimum of five spheres in each of the nine batches. Absorption was determined by measurement of diameter before and at fixed time intervals (1, 3, 9, 15 and 30 s) after addition of 100 μL phosphate buffer. A minimum of five spheres from each batch were measured and their volume was then calculated, assuming the DSM were completely spherical. Swelling of the microspheres occurs by diffusion of water into and hydration of the polymer, a process that continues towards equilibrium at maximum relaxation of the cross-linked starch chains. Consequently it may be assumed that the process follow Fick's diffusion with an initial rapid swelling rate that declines exponentially. The data may thus be explained by:

$$Y = Y_\infty (1 - e^{-kt})$$

wherein k is the first-order swelling constant and $Y_\infty$ is the volume increase at maximum swelling.

In-vitro Platelet Adhesion

To study the possible affinity/interaction between the various DSM batches and factors of known importance to the coagulation process, platelet adhesion to the different DSM batches was investigated. 450 μl of heparinised platelet-rich plasma was added to test tubes containing 1 μg DSM and thereafter agitated in an orbital shaker for 20 minutes at 500 rpm. Thereafter the DSM were thoroughly washed in PBS by repeatedly letting the DSM sediment to the bottom and exchange the supernatant with fresh PBS and thereafter vortex the tube. DSM-adhered platelets were then fixed with 3.7 PFA in PBS and permeabilised using 0.1% Triton-X in PBS, and finally fluorescently stained with Alexa 546-Phalloidin. Thorough rinsing was performed between each step in the procedure. Images of DSM and fluorescent platelets were acquired with an AxioObserver Z1 (Zeiss) fluorescence microscope and AxioVision (Zeiss) imaging software.

In vivo Pilot Study in an Experimental Renal Bleeding Model

The study was performed in accordance to the guidelines of good laboratory practice and approved by the Local University Ethics Committee for Animal Experiments. Three different batches of DSM were chosen based on the outcome of the in-vitro studies described above. One neutral batch, one that activated the coagulation and finally one batch with platelet adhesion properties were chosen for the in-vivo testing. The batches were blinded and randomised to the investigator performing the study. Twenty-one adult acclimatised male Sprauge-Dawley rats (median weight 342 g, iqr: 314-360) with free supply of food and water were anaesthetised (Hynorm, Janssen Pharma, Belgium and Midazolam Hameln, Pharma Hameln, GmbH). After catheterisation of the jugular vein (for IV injections) a transversal laparotomy was performed. The left kidney was dissected and the renal vessels were clamped two minutes after IV administration of Unfractionated Heparin (U H, LEO Pharma N S, Denmark) 200 IU/kg. The lateral one third of the kidney was then resected and 1 mL of randomised DSM applied on the raw kidney surface, manual compression started (with a gauze compress between the starch powder and the investigators finger) and the vessel clamp was removed. Compression remained for 2 minutes, then released for control of hemostasis. If bleeding occurred compression continued with hemostatic controls each minute. Primary hemostasis was defined as no visible bleeding within 20 minutes from renal resection. Animals obtaining hemostasis were observed another 20 minutes for possible re-bleeding. All animals were euthanised with an IV injection of phenobarbiturate acid and ethanol. Blood loss was collected and weighed. Study endpoints were: ability to obtain primary hemostasis, time to hemostasis, frequency of re-bleeding and blood loss.

Statistics

Descriptive data are presented with median values and individual or inter quartile range (iqr). Non-parametric test were performed, since the distribution of data was skewed. $\chi^2$ tests were performed for contingency tables and Kruskal-Wallis analysis of variance was used when unpaired data were compared. A p value of <0.05 was considered significant.

The software SPSS 17.0 for Mac and Windows (www.spss.com) was used.

Results

Modifications of DSM

Surface charges are given in table 2. The synthetic procedure was not optimised and carboxymethylation did not result in appreciable surface charge. Acetylation is not expected to change surface charge whereas the other methods should lead to significant positive and negative surface charges.

TABLE 2

The chemical modifications of the DSM and the outcome in measured charges.

| Batch: | Modification of DSM: | Size inclusion: | Charge: |
|---|---|---|---|
| 1 | N-octenyl succinic anhydride | — | 11.8 μequ/g anionic |
| 2 | Chloroacetic acid | — | 0.7 μequ/g anionic |
| 3 | Acetic anhydride | — | 0.3 μequ/g anionic |
| 4 | Diethylaminoethyl chloride | >80 μm | 459 μequ/g cationic |
| 5 | No surface modification | — | 0.5 μequ/g cationic |
| 6 | Ellagic acid[1] | — | NA |
| 7 | Diethylaminoethyl chloride | <80 μm | Not measured |
| 8 | Ellagic acid[2] | — | NA |
| 9 | Diethylaminoethyl chloride[3] | >150 μm | 100 μequ/g cationic |

[1]Dissolved in water
[2]Dissolved in ethanol
[3]More extensive crosslinking

Characterisation of Starch Spheres

Figure 2:
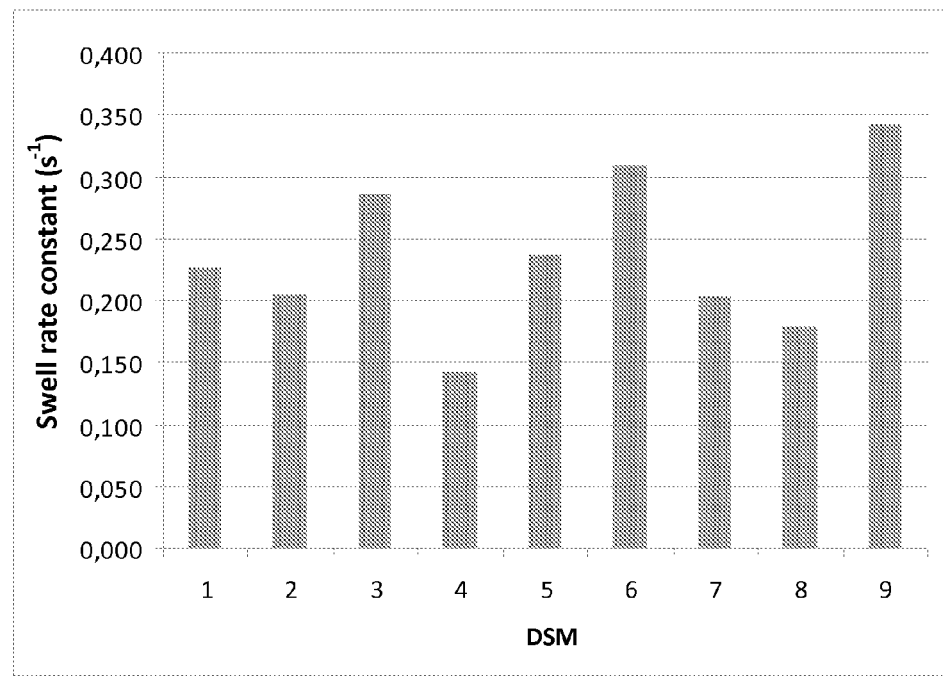
FIG. 2 illustrates that the swelling of the microspheres may be assumed to follow Fick's diffusion with an initial rapid swelling rate that declines exponentially.

There was a significant difference in dry diameter between the batches (p=0.006), batch 6 having the smallest size spheres (median diameter 54 μm, iqr: 38-58) and batch 2 the largest (median diameter 72 μm, iqr: 67-76). After addition of phosphate buffer all batches increased rapidly in volume (FIG. 2), and after 30 s they had expanded between 5 and 25 times their dry volume (table 3). The amount of swelling was significantly different between the batches (p=0.001).

TABLE 3

DSM dry volume and after 30 seconds in phosphate buffer solution.

| DSM Batch | Dry volume pL* | Volume pL* 30 s | Volume increase % |
|---|---|---|---|
| 1 | 157 (110-165) | 1123 (943-1150) | 700 (647-1000) |
| 2 | 195 (158-231) | 1047 (871-1629) | 600 (512-715) |
| 3 | 102 (79-128) | 775 | 760 (653-760) |
| 4 | 128 (120-180) | 1838 (1551-2187) | 1308 (1001-1559) |
| 5 | 88 (60-126) | 998 (688-1110) | 1071 (853-1264) |
| 6 | 82 (28-105) | 750 (439-1114) | 1058 (714-1311) |
| 7 | 166 (130-219) | 829 (760-1083) | 538 (371-751) |
| 8 | 113 (95-163) | 659 (599-875) | 619 (521-666) |
| 9 | 125 (92-249) | 3368 (1697-3368) | 2593 (2040-2593) |

*Median values (iqr), volume in pikoliter (1 pL = 1 ml$^{-9}$)

Platelet Stimulation

There was an evident adherence of platelets to DSM in three of the modified batches (No. 4, 7 and 9), whereas the rest of the DSM-batches did not affect platelets at all (FIG. 3). The results were confirmed using PRP from three different donors.

The Randomised, Blinded In vivo Pilot Experimental Study

All animals treated with batch 9 obtained primary hemostasis, compared to 14-43% primary hemostasis with the other batches (FIG. 4). Time to hemostasis also differed between the groups (p=0.044), batch 9 treated animals were fastest (median 2 min: iqr: 2-3:20) whereas batch 6 required median 6 min (n=3) and batch 5 10 min (n=1) before they ceased to bleed. Two batch 9 treated animals were the only re-bleeders (p=NS, compared to the other batches). Batch 9 treated animals had less blood loss (median 1 g, iqr: 0.4-1.2) compared to the other batches (batch 5: 5 g, 4.3-6.7, batch 6: 5.3 g, 2.2-8.6), p=0.001 (FIG. 5).

The postulated hemostatic effect of DSM by absorption of fluid (and small molecules) from the blood and concentrating endogenous coagulation factors on the spheres, may be dependent of a fast and considerable swelling of the microspheres. All batches in this study increased their volume rapidly after addition of phosphate buffer, but both the velocity and the total amount of swelling differed between the batches. Swelling depends on relaxation of the polyglucose chains as they are hydrated. This is restricted by many cross links and facilitated by charge repulsion of the ligands. We could find no clear correlations with the measured characteristics (e.g. charge), though. Low cross linking and high and fast swelling implicate rapid degradation and therefore the increase in volume will not be hazardous even if applied intra operatively in locations where space may become limited at the end of the procedure. In this study the rapid absorption of fluid and swelling of the DSM was not sufficient for hemostasis in vivo, only 1 of 7 animals obtained primary hemostasis treated with non-modified microspheres.

The DSM with superior hemostatic capacity in vivo proved to be those with platelet stimulating properties. Platelet adhered to the positively charged DSM, the diethylaminoethyl (DEAE) prepared batches (4, 7 and 9), which is in accordance with reported platelet adherence to surfaces exposing positive charged groups (Lee J H, Khang G, Lee J W, Lee H B. Platelet adhesion onto chargeable functional group gradient surfaces. J Biomed Mater Res 1998 May; 40(2):180-6). No objective quantification of amount of platelets that adhered to respective DEAE-modified batch was performed, but by ocular assessment there was no obvious difference in the amount of platelet adherence between batch 4, 7 and 9 , even if there was a measured difference in charge between batch 4 and 9. DEAE-chloride reacts with the hydroxylgroups on the DSM surface, generating DEAE groups that are positive at physical pH. DEAE ligands render microspheres that are non-biodegradable and probably unsuitable for human use. However, as a proof-of—concept to distinguish if the spheres can become platelet-adherent and whether this has any clinical hemostatic significance, the DEAE modification was valuable. A fast and efficient stimulation of platelets is crucial for instant hemostasis produced by a physical plug of aggregated platelets. The platelets are also required for efficient amplification and propagation of thrombin generation, a process strongly catalysed by the stimulated platelet surface, resulting in a fibrin network that stabilises the primary platelet plug.

The invention claimed is:

1. A biodegradable microsphere having a diameter of 10 to 2000 μm comprising cross-linked hydrolysed starch onto which a di-methyl glycine ligand has been directly coupled via a carboxylic ester bond formed between the carboxylic acid group of the di-methyl glycine ligand and a hydroxyl group of a glucose residue in the cross-linked hydrolysed starch, and wherein on average 0.05 to 1.5 di-methyl glycine ligands have been coupled to each glucose moiety in the hydrolysed starch, and wherein the di-methyl glycine ligands are biodetachable in vivo.

2. The microsphere according to claim 1, wherein the di-methyl glycine ligand has a physiologically active counter ion.

3. The microsphere according to claim 2 for use in hemostasis, wherein the microsphere has a mean diameter of 10-200 μm.

4. The microsphere according to claim 3, wherein the counter ion is ellagic acid.

5. A material for use in connection with wound healing comprising microspheres according to claim 1 in powder form, wherein the microspheres, upon administration to a wound, form a three-dimensional structure comprising voids between the microspheres, wherein the voids are at least 30 μm.

6. The material according to claim 5, wherein each microsphere is part of a homogenous size fraction with maximum variation of the mean diameter of ±15%.

7. The material according to claim 5, wherein the microspheres have a mean diameter of from 200 μm to 2000 μm.

8. The microsphere according to claim 1 for use in in vitro cell culture, wherein the microspheres have a mean diameter of from 200 μm to 1000 μm.

9. A wound dressing comprising the material according claim 5.

10. A method of carrying out hemostasis by topically or intraoperatively administering an effective amount of a microsphere according to claim 1 to a mammal suffering from a bleeding wound.

11. A method for carrying out wound healing by topically or intraoperatively adding an effective amount of a material according to claim 5 to a mammal suffering from a wound.

12. A method for in vitro cultivation of cells, wherein at least one microsphere according to claim 1 is added to a culture medium to which also the cells to be cultivated are added, the cells are then allowed to propagate.

13. A new biodegradable wound healing composition comprising:
- a plurality of biodegradable microspheres, each microsphere of the wound healing composition having a diameter of 10 to 2000 μm and cross-linked hydrolysed starch onto which a di-methyl glycine ligand has been directly coupled via a carboxylic ester bond formed between the carboxylic acid group of the di-methyl glycine ligand and a hydroxyl group of a glucose residue in the cross-linked hydrolysed starch, and
- wherein on average 0.05 to 1.5 di-methyl glycine ligands are coupled to each glucose moiety in the hydrolysed starch, and wherein the di-methyl glycine ligands are biodetachable in vivo.

* * * * *